United States Patent [19]

D'Silva

[11] 4,179,514
[45] Dec. 18, 1979

[54] KETOALKANESULFENYL AND KETOALKANETHIOSULFENYL CARBAMATES

[75] Inventor: Themistocles D. J. D'Silva, South Charleston, W. Va.

[73] Assignee: Union Carbide Corporation, New York, N.Y.

[21] Appl. No.: 867,368

[22] Filed: Jan. 6, 1978

Related U.S. Application Data

[62] Division of Ser. No. 688,410, May 20, 1976, Pat. No. 4,081,550.

[51] Int. Cl.$^2$ .................... A01N 9/12; C07C 149/12; C07C 149/20

[52] U.S. Cl. .................... 424/277; 424/246; 424/248.5; 424/270; 424/275; 424/276; 424/285; 424/298; 260/346.73; 260/453 RW; 260/453 RZ; 260/465 D; 260/465.4; 260/566 AC; 544/175; 548/184; 549/18; 549/19; 549/21; 549/28; 549/38; 549/39; 549/51; 549/68; 544/58.2

[58] Field of Search ............ 260/327 P, 327 M, 330.5, 260/453 RW, 453 RZ, 453; 424/298, 277, 276, 270, 246, 288.5, 286; 544/58, 175; 560/137, 161, 134, 138

[56] References Cited

U.S. PATENT DOCUMENTS

| | | | |
|---|---|---|---|
| 3,980,693 | 9/1976 | Kuhle et al. | 260/470 |
| 4,066,689 | 1/1978 | D'Silva | 260/544 C |
| 4,081,550 | 3/1978 | D'Silva | 424/298 |

FOREIGN PATENT DOCUMENTS

2357930 5/1975 Fed. Rep. of Germany.

*Primary Examiner*—John D. Randolph
*Attorney, Agent, or Firm*—Clement J. Vicari

[57] ABSTRACT

Ketoalkanesulfenyl and ketoalkanethiosulfenyl carbamates exhibit exceptional pesticidal activity.

47 Claims, No Drawings

KETOALKANESULFENYL AND KETOALKANETHIOSULFENYL CARBAMATES

This application is a division of our prior U.S. application: Ser. No. 688,410 filing date May 20, 1976, now U.S. Pat. No. 4,081,550, granted Mar. 28, 1978.

This invention relates to ketoalkanesulfenyl and ketoalkanethiosulfenyl carbamates, to their use in pesticidal compositions and for the control of certain economic pests.

More particularly, this invention relates to compounds of the formula:

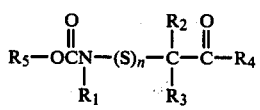

wherein:

n is 1 or 2;

$R_1$ is alkyl;

$R_2$ is alkyl or chlorine;

$R_3$ is hydrogen, alkyl, phenyl, alkoxycarbonyl, alkanoyl or phenoxycarbonyl;

$R_4$ is hydrogen, phenoxy, alkyl, alkoxy or phenyl;

$R_3$ and $R_4$ together may form an alkylene chain completing a five or six membered alicyclic ketone or dione;

$R_5$ is:

A. naphthyl, benzofuranyl, benzothienyl, indanyl or phenyl; or

B. phenyl substituted with one or more chloro, bromo, fluoro, nitro, cyano, alkyl, alkoxy, alkynyloxy, dioxalanyl, dialkylamino, alkoxycarbonylamino, dicyanoethylidene, alkylthio, alkylthioalkyl, alkylsulfinylalkyl, alkylsulfonylalkyl, dithiolanyl or dialkylaminemethyleneimino groups; or C. 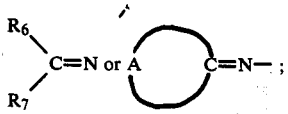

wherein:

$R_6$ and $R_7$ are individually hydrogen, cyano, chloro, alkyl, phenyl, alkylthio, alkylthioalkyl, alkylsulfinylalkyl, alkylsulfonylalkyl, cyanoalkyl, nitroalkyl, alkanoyl, cyanoalkylthio or aminocarbonylalkylthio groups; and A is a divalent alkylene chain completing a five or six membered alicyclic ring which includes up to three hetero atoms selected from among oxygen, sulfur, sulfinyl, sulfonyl, aminocarbonyl or alkylaminocarbonyl provided that not more than one of said hetero atoms may be aminocarbonyl or alkylaminocarbonyl.

The compounds of this invention exhibit outstanding miticidal and insecticidal activity. Certain of these compounds also exhibit excellent nematocidal activity. They are relatively non-toxic to plants and mammals when used in amounts sufficient to kill mites, insects and nematodes.

In general, $R_1$, $R_2$, $R_3$, $R_4$, $R_6$ and $R_7$ individually may not include more than 6 aliphatic carbons. Preferred because of their higher level of pesticidal activity are the compounds of this invention in which $R_1$ is methyl and the total number of aliphatic carbons included in any one $R_2$, $R_3$, $R_4$, $R_6$ and $R_7$ substituents does not exceed four.

This invention also relates to insecticidal, miticidal and nematocidal compositions comprising an acceptable carrier and an insecticidally, miticidally or nematocidally effective amount of a compound according to this invention. This invention also includes a method of controlling insects and mites by subjecting them to an insecticidally, nematocidally or miticidally effective amount of a compound according to this invention.

The compounds of this invention can be conveniently prepared by reacting the corresponding carbamoyl halide with an appropriately substituted phenol or oxime in the presence of a suitable acid acceptor as illustrated in the following reaction scheme:

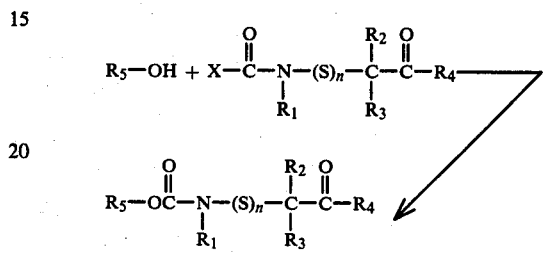

wherein $R_1$, $R_2$, $R_3$, $R_4$, $R_5$ and n are as described above and X is either chlorine or fluorine.

The reactants and an acid acceptor are brought together, preferably in an inert solvent. Any inert solvent may be used such as benzene, toluene, xylene, dioxane, tetrahydrofuran, ethyl ether, methylene chloride or the like. The acid acceptor employed can be either an organic or inorganic base. Inorganic bases such as sodium and potassium hydroxide and organic bases such as organic amines and alkali metal alkoxides may be used as acid acceptors. Preferred acid acceptors are tertiary amines, such as triethylamine, pyridine or 1,4-diazabicyclo [2.2.2] octane.

The reaction can be conducted in either a homogenous phase system or a heterogenous phase system. In the latter case, a phase transfer agent, such as crown ether and quaternary ammonium halide, can be used to facilitate the transfer of reactants across the phase interface.

Reaction temperatures are not critical and will vary widely depending to a large extent on the reactivity and stability of the reactants. In most cases the reaction goes to completion at room temperature. If reduced or extended reaction times are desired, the reaction can be conducted at a temperature of from about 0° C. to about 100° C.

Reaction pressures are not critical. Preferably, the reaction will be conducted at atmospheric or autogeneous pressure.

Naphthol, benzofuranol, benzothienol, indanol and phenol precursors are well known compounds which can either be obtained from commercial sources or prepared by well known conventional methods.

Linear oxime precursors of the formula:

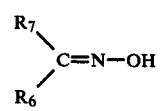

in which $R_7$ and $R_6$ are as described above, can be conveniently prepared according to a variety of methods. For example, substituted and unsubstituted linear oximes can be prepared by the methods disclosed in U.S. Pat. Nos. 3,843,669, 3,217,036, 3,217,037, 3,400,153, 3,536,760 and 3,576,834.

Alicyclic oxime precursors, of the formula:

used in the preparation of the novel carbamate compounds of this invention can be prepared by a variety of methods, the choice of method being influenced to a large extent by the types and number of hetero groups included within the alicyclic ring. For example:

A. 1,3,5-trithiane, 1,3,5-oxadithiane and 1,4-oxazine-3-one oxime compounds can be conveniently prepared by sequentially treating the corresponding 1,3,5-trithiane, 1,3,5-oxadithiane or 1,4-oxazin-3-one compound with an alkali metal alkoxide and an alkyl nitrite ester, in an aprotic solvent, followed by the addition of a neutralizing acid. For example, 2-oximino-4-methyltetrahydro-1,4-oxazin-3-one can be prepared by treating 4-methyltetrahydro-1,4-oxazin-3-one with potassium t-butoxide followed by the addition of isobutyl nitrite. The reaction is conducted in anhydrous tetrahydrofuran. After the reaction has gone to completion in about 3 hours the resulting oxime salt can be neutralized with hydrochloric acid.

B. Tetrahydrothiazine-3-one oxime compounds can be prepared by reacting ethoxycarbonylformhydroamoyl chloride with the sodium salt of an appropriately substituted alkylaminoalkane mercaptan in an aprotic solvent, such as benzene, chloroform and the like. This reaction is described in more detail in U.S. Pat. No. 3,790,560.

C. Oxathiane or oxathiolane oxime compounds can be prepared according to the method disclosed in Belgium Pat. No. 813,206 and U.S. Pat. application Ser. No. 347,446 filed Apr. 3, 1973.

D. 1,3-dithiolane and 1,4-dithiane oxime compounds can be prepared by reacting equivalent amounts of 2-haloalkanehydroxamoyl halide with the sodium salt of an appropriately substituted alkanedithiol in an aprotic solvent like benzene, methylene chloride or ethanol. For example, 2-oximino-3,3-dimethyl-1,4-dithiane can be prepared by adding 1,2-ethanedithiol to sodium ethoxide, thereby producing the sodium salt of 1,2-ethanedithiol in situ, and then adding to the reaction mixture 2-chloro-2-methylpropionhydroxamoyl chloride.

Compounds of this invention in which $R_5$, $R_6$ and $R_7$ are alkylsulfinylalkyl or alkylsulfonylalkyl and in which A includes a sulfinyl or a sulfonyl can be prepared by the selective oxidation of the corresponding thio compound at an appropriate point in the synthetic procedure. For example, compounds of this invention in which A includes sulfinyl or sulfonyl groups can be prepared by the selective oxidation of the corresponding sulfur carbamate compound with peracetic acid subsequent to carbamoylation or by selectively oxidising the corresponding oxime compound with peracetic acid prior to carbamoylation.

The carbamoyl halide precursors employed in the preparation of the compounds of this invention can be prepared according to a variety of conventional synthesis methods. For example, the corresponding N-chlorothiocarbamoyl halide can be reacted with an appropriately substituted ketone having an alpha hydrogen to produce the N-alkyl-N-(ketoalkanesulfenyl) carbamoyl halide; an appropriate mono substituted N-alkyl carbamoyl fluoride can be reacted with the corresponding α-chlorothiosulfenyl ketone in the presence of an acid acceptor, such as triethylamine, pyridine and the like, to produce the N-alkyl-N-(ketoalkanethiosulfenyl) carbamoyl fluoride; N-chlorothiocarbamoyl halide can be reacted with an appropriately substituted α-diazoketo compound to produce the N-alkyl-N-(α-chloroketoalkanesulfenyl)carbamoyl halide; or the corresponding N-chlorothiocarbamoyl halide can be reacted with an appropriately substituted mercaptan to produce the N-alkyl-N-(ketoalkanethiosulfenyl)-carbamoyl chloride. Each of the above disclosed reactions can be conducted under essentially identical reaction conditions. Generally, the reactants are contacted in an aprotic solvent. Any aprotic solvent including benzene, chloroform and the like can be used. Reaction temperatures and pressures are not critical. The reactions are usually conducted at atmospheric or autogenous pressure. The reactions can be conducted at a temperature of from about $-30°$ C. to about $100°$ C. The above disclosed methods are described in detail in my co-pending United States Patent Application Ser. No.     , entitled Ketoalkanesulfenylcarbamoyl and Ketoalkanethiosulfenylcarbamoyl Halides, filed concurrently herewith.

The following specific examples are presented to more particularly illustrate the invention.

EXAMPLE I

Preparation of 1-Methylthioacetaldehyde O-[N-methyl-N-(2,4-dimethyl-3-oxo-2-pentanesulfenyl)carbamoyl]oxime

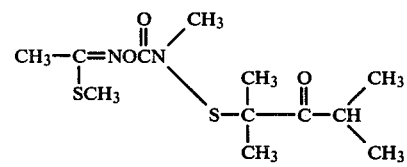

To a solution of 2.1 g (0.02 m) of 1-methylthioacetaldoxime and 5.0 g (0.02 m) of N-methyl-N-(2,4-dimethyl-3-oxo-B 2-pentanesulfenyl)carbamoyl chloride in 100 ml of dioxane, was added dropwise with stirring 2.02 g (0.02 m) of triethylamine. After allowing the reaction mixture to stand at ambient temperature for 16 hours it was diluted with water and extracted in ethyl acetate. The organic extract was dried over magnesium sulfate and concentrated under reduced pressure. The residual oil was predominantly the product contaminated with the unreacted oxime. The product was purified by column chromatography using silica gel to yield 0.88 g of an oil.

IR (Neat) 5.88 and 6.0μ. NMR(CDCl$_3$)δ1.14, (d), J=7.0Hz, 6H; 1.48 (s), 6H, 2.99 (s), 3H; 2.45 (s), 3H; 3.19 (s), 3H; 3.0–3.5 (broad) 1H.

Calc'd for $C_{12}H_{22}N_2O_3S_2$: C, 47.03; H, 7.24; N, 9.14. Found: C, 46.94; H, 7.11; N, 9.01.

EXAMPLE II

Preparation of 1Isopropylthioacetaldehyde O-[N-methyl-N-(2,4-dimethyl-3-oxo-2-pentanesulfenyl)carbamoyl]oxime

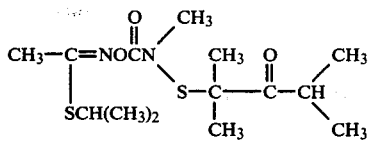

Prepared as in Example I by reacting 5.06 (0.0375 m) of 1-isopropylthioacetaldoxime, 9.39 g (0.0375 m) of approximately 95 percent pure N-methyl-N-(2,4-dimethyl-3-oxo-2-pentanesulfenyl)carbamoyl chloride and 3.79 g (0.0375 m) of triethylamine in 100 ml of dioxane. The product crystallized from pentane to yield 2.55 g of a white solid, m.p. 79°–81° C.

Calc'd for $C_{14}H_{26}N_2O_3S_2$: C, 50.27; H, 7.83; N, 8.38. Found: C, 50.48; H, 7.46; N, 8.43.

EXAMPLE III

Preparation of 2-Methylthio-2-methylpropionaldehyde O-[N-methyl-N-(2,4-dimethyl-3-oxo-2-pentanesulfenyl)carbamoyl]oxmine.

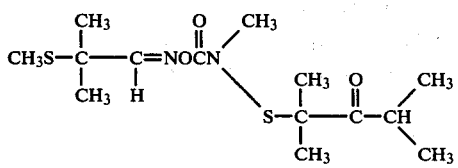

Prepared as in Example 1 by reaction 2.66 g (0.02 m) of 2-methylthio-2-methylpropionaldoxime, 5.0 g (0.02 m) of 95 percent N-methyl-N-(2,4-dimethyl-3-oxo-2-pentanesulfenyl)carbamoyl chloride and 2.02 g (0.02 m) of triethylamine in 100 ml of dioxane. The crude residual oil was purified by column chromatography to yield 1.2 g of a light yellow oil.

IR (Neat) 5.85 and 5.98μ. NMR(CDCl$_3$)δ1.14 (d) J=7.0Hz,6H; 1.48 (s), 12H; 1.99 (s), 3H; 3.22 (s), 3H; 7.53 (s) 1H.

Calc'd for $C_{14}H_{26}N_2O_3S_2$; C, 50.27; H, 7.83; N, 8.37. Found: C, 51.80; H, 7.84 N, 8.21.

EXAMPLE IV

Preparation of 2-Nitro-2-methylpropionaldehyde O-[N-methyl-N-(2,4-dimethyl-3-oxo-2-pentanesulfenyl)carbamoyl]oxime

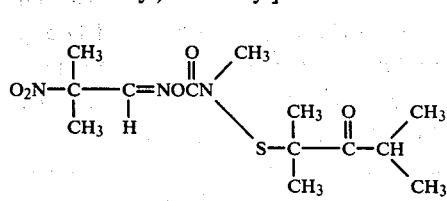

Prepared as in Example 1 by reacting 2.78 g (0.021 m) of 2-nitro-2-methylpropionaldoxime, 5.0 g (0.21 m) of N-methyl-N-(2,4-dimethyl-3-oxo-2-pentanesulfenyl)-carbamoyl fluoride and 2.13 g (0.021 m) of triethylamine in 50 ml of dioxane. The product was purified by column chromatography to yield 0.55 g of an oil.

IR (Neat) 5.74, 5.9μ (C=O). NMR (CDCl$_3$)δ1.13 (d), J=7.0Hz, 6H; 1.48 (s), 6H; 1.85 (s), 6H; 3.25 (s), 3H; 3.0–3.5(m), 1H; 8.10 (s), 1H.

Calc'd. for $C_{13}H_{23}N_3O_5S$: C, 46.83; H, 6.95; N, 12.60. Found: C, 46.46; H, 6.95; N, 12.07.

EXAMPLE V

Preparation of 2-[[O-[N-methyl-N-(2,4-dimethyl-3-oxo-2-pentanesulfenyl)carbamoyl]oximino]]-1,4-dithiane

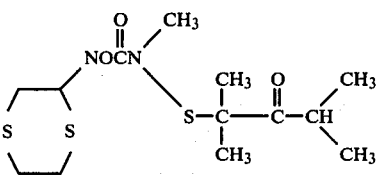

Prepared as in Example 1 by reacting 8.0 g (0.053 m) of 2-oximino-1,4-dithiane, 15.2 g (0.058 m) of N-methyl-N-(2,4-dimethyl-3-oxo-2-pentanesulfenyl)carbamoyl chloride and 5.42 g (0.053 m) of triethylamine in 100 ml of dioxane. The product crystallized from isopropyl ether-ethyl acetate to yield 4.3 g of a white solid, (m.p. 80°–82° C.) Recrystallization raised the melting point to 85°–86° C.

Calc'd. for $C_{13}H_{22}N_2O_3S_3$: C, 44,54; H, 6.33; N, 7.99. Found: C, 44.62; H, 6.14; N, 8.03.

EXAMPLE VI

Preparation of 4-[[O-[N-methyl-N-(2,4-dimethyl-3-oxo-2-pentanesulfenyl)carbamoyl]oximino]]-5-methyl-1,3-oxathiolane

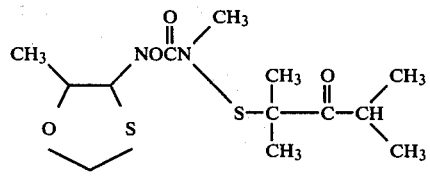

Prepared as in Example I by reacting 2.64 g (0.02 m) of 5-methyl-4-oximino-1,3-oxathiolane, 4.47 g (0.02 m) of N-methyl-N-(2,4-dimethyl-3-oxo-2-pentanesulfenyl)-carbamoyl chloride and 2.02 g (0.02 m) of triethylamine in 25 ml of dioxane. Crystallized from isopropyl etherto yield 1.2 g of a white solid, m.p. 90°–92° C.

Calc'd for $C_{13}H_{22}N_2O_4S_2$: C, 46.68; H, 6.63; N, 8.38. Found: C, 46.48; H, 6.41; N, 8.37.

EXAMPLE VII

Preparation of 2-[O-[N-methyl-(2,4-dimethyl-3-oxo-2-pentanesulfenyl)carbamoyl]oximino]-3,5,5-trimethylthiazolidin-4-one

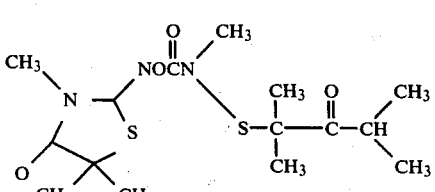

Prepared as in Example I by reacting 2.94 g (0.0169 m) of 3,5,5-trimethyl-2-oximino-thiazolidin-4-one, 4.0 g (0.0169 m) of N-methyl-N-(2,4-dimethyl-3-oxo-2-pentanesulfenyl)carbamoyl chloride and 1.7 g (0.0169 m) of triethylamine in 200 ml of dioxane. The productcrystallized from isopropyl ether to yield 2.5 g of a white solid, m.p. 112°–114° C.

Calc'd. for $C_{15}H_{25}N_3O_4S_2$: C, 47.98; H, 6.71; N, 11.19. Found: C, 48.00; H, 6.45; N, 11.15.

EXAMPLE VIII

Preparation of 2-[[O-[N-methyl-N-(2-methyl-1-oxo-2-cyclopentanesulfenyl)carbamoyl]oximino]]-3,5,5-trimethylthiazolidin-4-one

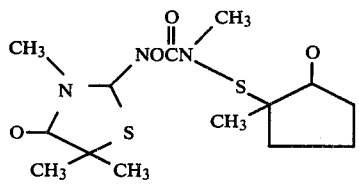

To a solution of 3.93 g (0.0225 m) of 3,5,5-trimethyl-2-oximino-thiazolidin-4-one and 2.28 g (0.0225 m) of triethylamine in 75 ml of dioxane was added dropwise with stirring 5.0 g (0.0225 m) of N-methyl-N-(2-methyl-1-oxo-2-cyclopentanesulfenyl)carbamoyl chloride whilst maintaining the temperature between 10°–15° C. The reaction mixture was left standing for 16 hours at 5° C., and then diluted with ice water. The product was extracted in ethylacetate, dried and concentrated to yield 0.66 g of white solid, m.p. 119°–121° C.

Calc'd. for $C_{14}H_{21}N_3O_4S_2$: C, 46.77; H, 5.89; N, 11.69. Found: C, 46.35; H, 5.88; N, 11.42.

EXAMPLE IX

Preparation of 2-[[O-[N-methyl-N-(2-benzoyl-2-propanesulfenyl)carbamoyl]oximino]]-3,5,5-trimethylthiazolidin-4-one

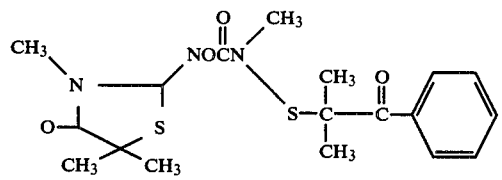

To a solution of 2.5 g (0.015 m) of 3,5,5-trimethyl-2-oximino-thiazolidin-4-one and 3.93 g (0.015 m) of N-methyl-N-(2-benzoyl-2-propanesulfenyl)carbamoyl chloride in 100 ml of dioxane was added 1.5 g (0.015 m) of triethylamine. After stirring at room temperature for 16 hours, the reaction mixture was diluted with water and the product isolated in ethylacetate. Recrystallized from isopropyl ether. Weight of the procut 1.3 g, m.p. 98°–100° C.

Calc'd for $C_{18}H_{23}N_3O_4S_2$: C, 52.79; H, 5.66; N, 10.26. Found: C, 52.05; H, 5.59; N, 10.59.

EXAMPLE X preparation of 2-[[O-[N-methyl-N-(3-formyl-3-pentanesulfenyl)carbamoyl]oximino]]-3,5,5-trimethylthiazolidin-4-one

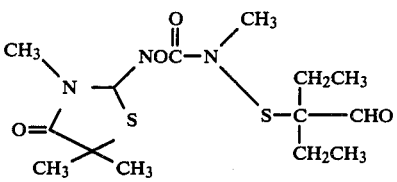

To a solution of 8.7 g (0.05 m) of 3,5,5-trimethyl-2-oximinothiazolidin-4-one and 8.9 g (0.05 m) of a 90 percent solution of N-methyl-N-(3-formyl-3-pentanesulfenyl)carbamoyl chloride in 150 ml of dioxane was added 5.04 g (0.05 m) of triethylamine. The reaction mixture was stirred at room temperature for 90 hours, and then added 300 ml of cold water. The solid formed was collected and taken in isopropyl ether and chloroform and chilled. Weight of the solid precipitate 3.5 g. Analytical sample, m.p. 105°–106° C.

Calc'd for $C_{14}H_{23}N_3O_4S_2$: C, 46.52; H, 6.41; N, 11.62. Found: C, 46.81; H, 6.11; N, 11.67.

EXAMPLE XI

Preparation of 2-[[O-[N-methyl-N-(bis-ethoxycarbonylchloromethanesulfenyl)carbamoyl]oximino]]-3,5,5-trimethylthiazolidin-4-one

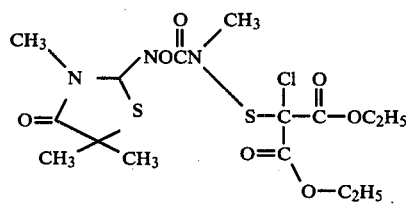

A mixture of 1.91 g (0.011 m) of 3,5,5-trimethyl-2-oximinothiazolidin-4-one, 5.0 g (0.011 m) of a 70 percent solution of N-methyl-N-(bis-ethoxycarbonylchloromethanesulfenyl)carbamoyl chloride and 1.11 g (0.011 m) of triethylamine in 100 ml of dioxane was stirred overnight at room temperature. The reaction mixture was diluted with water, the product was extracted into ethylacetate and the organic phase was washed with water, and dried over magnesium sulfate. Removal of the solvent gave a residual oil which was purified by chromatography through silica gel.

IR (Neat) 5.9μ (C=O). NMR(CDCl$_3$)δ1.36 (t), J=7.0Hz, 6H; 1.68 (s), 6H; 3.29 (s) 3H; 3.46 (s) 3H; 4.36 (q), j=7.0Hz, 4H.

EXAMPLE XII

Preparation of α-Cyanobenzaldehyde
O-[N-methyl-N-(2,4-dimethyl-3-oxo-2-pentanesulfenyl)-carbamoyl]oxime

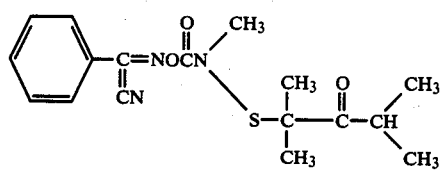

A mixture of 1.68 g (0.01 m) of sodium salt of α-cyanobenzaldoxime, 2.37 g (0.01 m) of N-methyl-N-(2,4-dimethyl-3-oxo-2-pentanesulfenyl) carbamoyl chloride in 75 ml of benzene was stirred at room temperature for 4 days. The mixture was washed with water and dried over magnesium sulfate. Removal of the solvent gave 2.65 g of a residual oil. Crystallized from isopropyl ether methylene chloride. m.p. 129°–130° C.

Calc'd for $C_{17}H_{21}N_3O_3S$: C, 58.77; H, 6.09; N, 12.09. Found: C, 58.00; H, 5.92; N, 11.95.

EXAMPLE XIII

Preparation of
7-[N-methyl-N-(2,4-dimethyl-3-oxo-2-pentanesulfenyl)-carbamoyloxy]-2,2-dimethyl-2,3-dihydrobenzofuran

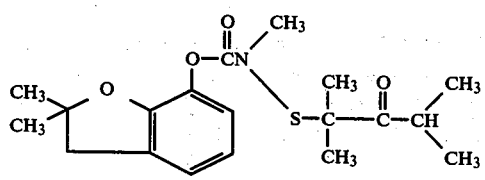

To a solution of 3.38 g (0.02 m) 2,2-dimethyl-2,3-dihydrobenzofuran-7-ol and 4.79 g (0.02 m) of N-methyl-N-(2,4-dimethyl-3-oxo-2-pentanesulfenyl)carbamoyl chloride in 15 ml of dioxane was added dropwise with stirring 2.2 g (0.021 m) of triethylamine. The spontaneous exotherm raised the temperature of the mixture from 23° C. to 30° C. The reaction mixture was stirred at room temperature for 24 hours and then diluted with water. The product was extracted in ethylacetate and the organic phase was washed in turn with sodium carbonate solution and water, and dried over magnesium sulfate. Removal of the solvent yielded 7.0 g of a viscous oil. On addition of pentane 0.5 g of carbofuran was isolated. The residual filtrate comprised predominantly of the desired product.

Infra-red (Neat) 5.75, 5.85μ (Shoulder), C=O. NMR(CDCl$_3$)δ1.1, (d), J=7.0Hz, 6H; 1.41, (s), 6H; 1.5 (s), 6H; 2.95 (s), 2H; 3.25 (s), 3H; 6.6–7.1 (m) 3H.

Calc'd for $C_{19}H_{27}NO_4S$: C, 62.44; H, 7.45; N, 3.83. Found: C, 60.88; H, 7.07; N, 3.70.

EXAMPLE XIV

Preparation of
1-[N-methyl-N-(2,4-dimethyl-3-oxo-2-pentanesulfenyl)-carbamoyloxy]-napthalene

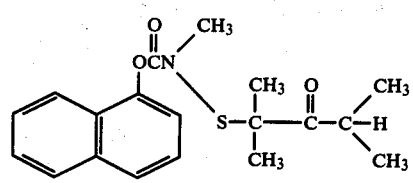

To a solution of 10.0 g (0.042 m) of N-methyl-N-(2,4-dimethyl-3-oxo-2-pentanesulfenyl)carbamoyl chloride and 6.06 g (0.042 m) of 1-naphthol in 75 ml of dioxane was added 4.26 g (0.042 m) of triethylamine. After stirring at room temperature for 17 hours the reaction mixture was diluted with 500 ml of cold water and the product taken into ethyl acetate. The organic phase was washed in turn with 1.0 percent sodium hydroxide and water and then dried over magnesium sulfate. On removal of the solvent it yielded 9.4 g of a residual oil.

Infra-red (Neat) 5.8, 5.88μ (Shoulder) C=O. NMR(CDCl$_3$)δ1.0, (d) J=7.0Hz, 6H; 1.41 (s), 6H; 3.30 (s), 3H; 7.2–8.1 (m), 7H.

Calc'd for $C_{19}H_{23}NO_3S$: C, 66.06; H, 6.71; N, 4.05. Found: C, 65.25; H, 6.28; N, 4.03.

EXAMPLE XV

Preparation of 1-Methylthioacetaldehyde
O-[N-methyl-N-(2,4-dimethyl-3-oxo-2-pentanethiosulfenyl)carbamoyl]oxime

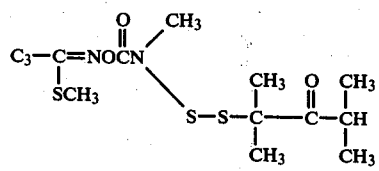

To a solution of 5.0 g (0.0476 m) of 1-methylthioacetaldoxime and 12.01 g (0.0476 m) of N-methyl-N-(2,4-dimethyl-3-oxo-2-pentanethiosulfenyl)carbamoyl fluoride in 75 ml of dioxane, was added 4.8 g (0.0476 m) of triethylamine. After stirring at room temperature for 18 hours the reaction mixture was diluted with 100 ml of water and the product was extracted in ethyl acetate. The organic extract was washed in turn with aqueous sodium bicarbonate solution and water. Dried over magnesium sulfate and concentrated. The product crystallized from isopropylether and hexane solution to yield 8.1 g of a white solid, m.p. 74°–75° C.

Calc'd for $C_{12}H_{22}N_2O_3S_3$: C, 42.57; H, 6.55; N, 8.28. Found: C, 42.71; H, 6.64; N, 8.29.

EXAMPLE XVI

Preparation of 1-Isopropylthioacetaldehyde O-[N-methyl-N-(2,4-dimethyl-3-oxo-2-pentanethiosulfenyl)carbamoyl]oxime

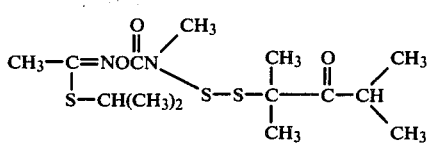

To a solution of 5.0 g (0.0375 m) of 1-isopropylthioacetaldoxime and 9.5 g (0.0375 m) of N-methyl-N-(2,4-dimethyl-3-oxo-2-pentanethiosulfenyl)carbamoyl fluoride in 75 ml of dioxane, was added 3.79 of (0.375 m) of triethylamine. The reaction mixture was stirred at room temperature for 24 hours. Isolation of the product in the usual way described previously, yielded 3.6 g of a crystalline solid, m.p. 66°–67° C.

Calc'd for $C_{14}H_{26}N_2O_3S_3$: C, 45.87; H 7.15; N, 7.64. Found: C, 45.99; H, 7.31; N, 7.64.

EXAMPLE XVII

Preparation of 4-[[O-[N-Methyl-N-(2,4-dimethyl-3-oxo-2-pentanethiosulfenyl)carbamoyl]oximino]]-5-methyl-1,3-oxathiolane

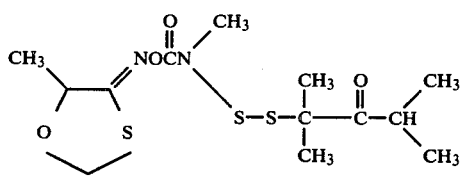

Prepared as in Example XV by reacting 4.99 g (0.0375 m) of 5-methyl-4-oximino-1,3-oxathiolane, 9.5 g (0.375 m) of N-methyl-N-(2,4-dimethyl-3-oxo-2-pentanethiosulfenyl) carbamoyl fluoride and 3.79 g (0.0375 M) of triethylamine in 75 ml of dioxane. Weight of the residual oil 7.0 g. 1R (Neat) 5.72 and 5.85μ(C=O).

NMR (CDCl₃)δ1.06 (d), J=7.0Hz, 6H; 1.57 (d), J=6.0Hz, 3H; 1.58 (s), 6H; 2.9-3.5(m), J=7.0Hz, 1H; 3.19 (s), 3H; 4.71(q) J=6.0 Hz, 1H; 5.22 (d), J=6.5Hz, 5.38 (d), J=6.5Hz, 2H.

Calc'd. for $C_{13}H_{22}N_2O_4S_3$: C, 42.6; H, 6.05; N, 7.64. Found: C, 42.53; H, 6.10; N, 7.84.

EXAMPLE XVIII

Preparation of 1-(2-Cyanoethylthio)acetaldehyde O-[N-methyl-N-(2,4-dimethyl-3-oxo-2-pentanethiosulfenyl)carbamoyl]oxime

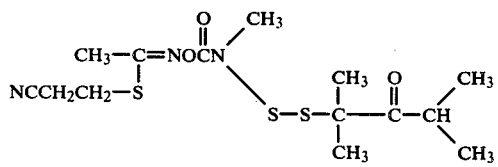

Prepared as in Example XV by reacting 5.41 g (0.0375 m) of 1-(2-cyanoethylthio)acetaldoxime, 9.5 g (0.0375 m) of N-methyl-N-(2,4-dimethyl-3-oxo-2-pentanethiosulfenyl) carbamoyl fluoride and 3.79 g (0.0375 m) of triethylamine in 75 ml of dioxane, m.p. 45°–48° C.

Calc'd for $C_{14}H_{23}N_3O_3S_3$: C, 44.54; H, 6.14; N, 11.13. Found: C, 44,64; H, 6.50; N, 11.14.

EXAMPLE XIX

Preparation of 1-Methylthioacetaldehyde O-[N-methyl-N-(2-benzoyl-2-propanethiosulfenyl)carbamoyl]oxime

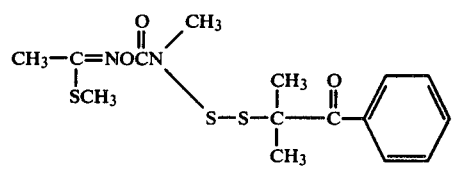

Prepared as in Example XV by reacting 10.5 g (0.1 m) of 1-methylthioacetaldoxime, 28.74 g (0.1 m) of N-methyl-N-(2-benzoyl-2-propanethiosulfenyl)carbamoyl fluoride and 10.19 g (0.1 m) of triethylamine in 100 ml of dioxane. Yield 9.48 g of white solid, m.p. 80°–82° C.

Calc'd. for $C_{15}H_{20}N_2O_3S_3$: C, 48.38; H, 5.41; N, 7.52. Found: C, 48.34; H, 5.67; N, 7.44.

EXAMPLE XX

Preparation of N-Methyl-N-(2,4-dimethyl-3-oxo-2-pentanesulfenyl)-carbamoyl chloride

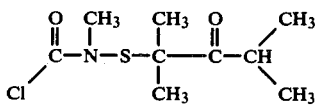

N-Methyl-N-chlorothiocarbamoyl chloride (3.2 g, 0.02 m) was added to 2.28 g (0.02 m) of diisopropyl ketone. The spontaneous exotherm raised the temperature to 35° C. After standing for 1 hour the dissolved hydrogen chloride was removed by warming the mixture under reduced pressure. Weight of the residual oil 4.0 g. $N_D^{23}$1.4947. Infra-red (Neat) 5.82, 5.92μ(carbonyl). NMR(CDCl₃)α1.15(d). J=7.0Hz, 6H; 1.55 (s), 6H; 3.22 (s), 3H; 3.0–3.5 (m). 1H.

EXAMPLE XXI

Preparation of N-Methyl-N-(2-formyl-2-propanesulfenyl)carbamoyl chloride

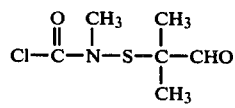

A solution of 1.6 g (0.01 M) N-Methyl-N-chlorothiocarbamoyl chloride in 20 ml of methylene chloride was added to a solution of 1.58 g (0.01 m) of isobutyraldehyde and the reaction mixture heated to 35° C. for 0.5 hr. The solvent was removed under reduced pressure to yield 1.7 g of an yellow oil.

Infra-red (Neat) 5.82μ (C=O). NMR(CDCl₃)α1.41 (s). 6H; 3.37 (s), 3H, 9.45 (s). 1H.

EXAMPLE XXII

Preparation of N-Methyl-N-(3-formyl-3-pentanesulfenyl)carbamoyl chloride

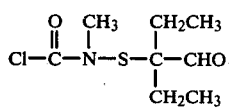

A solution of 1.6 g (0.01 m) of N-Methyl-N-chlorothiocarbamoyl chloride in 25 ml of methylene chloride was added dropwise to a stirred solution of 2.2 g (0.022 m) of 2-ethylbutyraldehyde in 25 ml of methylene chloride. The mixture was warmed to 40° C. for 2 hrs. After the evolution of hydrogen chloride had ceased, the solvent was removed under vacuum to yield 2.19 g of an oil.

Infra-red (Neat) 5.85μ (C=O). NMR(CDCl$_3$)α0.95 (t), J=7.0 H$_Z$, 6H; 1.75 (m). J=7.0 H$_Z$, 4H; 3.36 (s), 3H; 9.49 (s), 1H.

EXAMPLE XXIII

Preparation of N-Methyl-N-(3-formyl-3-heptanesulfenyl)carbamoyl chloride

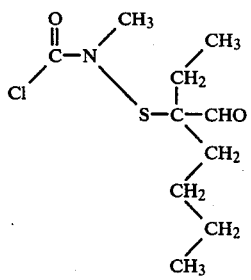

N-Methyl-N-chlorothiocarbamoyl chloride 1.6 g, (0.01 m) was added to 1.28 g (0.01 m) of 2-ethylhexaldehyde. The spontaneous exotherm raised the temperature of the mixture from 24° C. to 32° C. with evolution of hydrogen chloride. After stirring for 1 hour the dissolved gas was removed under reduced pressure to yield 2.4 g of a residual oil.

Infra-red (Neat) 5.8 (C=O)μ. NMR(CDCl$_3$)α1.0 (t). J=7.0H$_Z$, 6H; 1.0-2.0 (m), 8H; 3.34 (s), 3H; 9.47 (s), 1H.

EXAMPLE XXIV

Preparation of N-Methyl-N-(1-chloro-2-formyl-2-propanesulfenyl)carbamoyl chloride

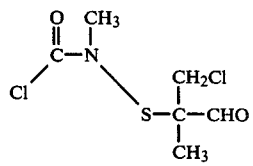

N-Methyl-N-chlorothiocarbamoyl chloride 8.0 g, (0.05 m) was added dropwise at 5° to 10° C. to 3.89 g (0.05 m) of methacrolein over a period of 10 minutes. After stirring for 1 hour the reaction mixture was kept under vacuum to remove volatile materials. Weight of the residual oil was 10.8 g.

Infra-red (Neat) 5.9 (C=O)μ. NMR(CDCl$_3$)α1.46 (s), 3H; 3.40 (s), 3H; 3.87 (d), J$_{AB}$=12.0 H$_Z$ and 4.08 (d). J$_{BA}$=12.0 H$_Z$, 2H; 9.52 (s), 1H.

EXAMPLE XXV

Preparation of N-Methyl-N-(2-benzoyl-2-propanesulfenyl)carbamoyl chloride

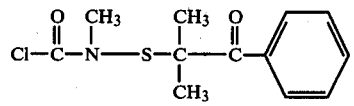

A mixture of 14.8 g (0.1 m) of isobutyrophenone and 16.0 g (0.1 m) of N-methyl-N-chlorothiocarbamoyl chloride was heated slowly to 30° C. whilst stirring. The exothermic reaction raised the temperature to 42° C. with evolution of hydrogen chloride. After stirring for 0.5 hours at 40° C. the residual hydrochloric acid was removed under reduced pressure. Weight of the residual oil 27.0 g.

Infra-red (Neat) 5.78, 5.98μ (C=O). NMR(CDCl$_3$)α1.6 (s), 6H; 3.30 (s), 3H; 7.3-8.1 (m), 5H.

EXAMPLE XXVI

Preparation of N-Methyl-N-(2-methyl-1-oxo-2-cyclopentanesulfenyl)-carbamoyl chloride

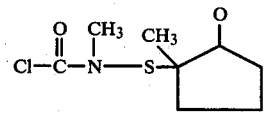

To a solution of 4.85 g (0.05 m) of 2-Methylcyclopentanone in 100 ml of methylene chloride cooled to 10° C. was added dropwise with stirring 8.0 g (0.05 m) of N-methyl-N-chlorothiocarbamoyl chloride over a period of 10 min. After stirring at 15° C. for 0.5 hours, the solvent was removed under reduced pressure to yield 10.0 g of a residual oil.

Infra-red (Neat) 5.8μ (C=O). NMR(CDCl$_3$)α1.53 (s), 3H; 1.9-2.7 (m). 6H; 3.38, (s), 3H.

EXAMPLE XXVII

Preparation of N-Methyl-N-(1-carboethoxy-1-chloromethanesulfenyl)carbamoyl chloride

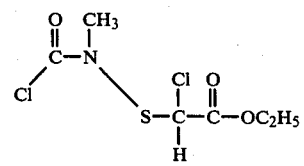

To a solution of 2.35 g (0.02 m) of ethyldiazoacetate in 50 ml of anhydrous ethyl ether, cooled to −10° C., was added dropwise with stirring 3.2 g (0.02 m) of N-methyl-N-chlorothiocarbamoyl chloride dissolved in 25 ml of ethyl ether, over a period of 15 min. After stirring for an additional 45 minutes and the evolution of nitrogen had ceased, the solvent was removed under reduced pressure to yield 4.8 g of an oil.

Infra-red (Neat) 5.8μ (C=O). NMR(CDCl$_3$)α1.35 (t), J=7.0H$_Z$, 3H; 3.55 (s), 3H; 4.33 (q), J=7.0H$_Z$, 2H; 5.62 (s), 1H.

The following compounds are representative of other compounds that are within the scope of this invention which can be prepared according to this invention by selecting appropriate starting materials for use in the procedures described above:

1-Methylthioacetaldehyde O-[N-methyl-N-(2,4,4-trimethyl-3-oxo-2-pentanesulfenyl)carbamoyl]oxime.
1-Methylthioacetaldehyde O-[N-methyl-N-(bis-ethoxycarbonylchloromethanesulfenyl)carbamoyl]oxime.
1-Methylthioacetaldehyde O-[N-methyl-N-(2,6,6-trimethyl-1-oxo-2-cyclohexanesulfenyl)carbamoyl]oxime.
1-(2-Cyanoethylthio)acetaldehyde O-[N-methyl-N-(2,4-dimethyl-3-oxo-2-pentanesulfenyl)carbamoyl]oxime.
1-(2-Cyanoethylthio)acetaldehyde O-[N-methyl-N-(2-methyl-1-oxo-2-cyclopentanesulfenyl)carbamoyl]oxime.
1-(2-Cyanoethylthio)acetaldehyde O-[N-methyl-N-(2-benzoyl-2-propanesulfenyl)carbamoyl]oxime.
2-Cyano-2-methylpropionaldehyde O-[N-methyl-N-(2,4-dimethyl-3-oxo-2-pentanesulfenyl)carbamoyl]oxime.
1-Methylthio-3,3-dimethyl-2-butanone O-[N-methyl-N-(2,4-dimethyl-3-oxo-2-pentanesulfenyl)carbamoyl]oxime.
2-[[O-[N-Methyl-N-(2,4-dimethyl-3-oxo-2-pentanesulfenyl)carbamoyl]oximino]]-1,3-dithiolane.
2-[[O-[N-Methyl-N-(2-methyl-1-oxo-2-cyclohexanesulfenyl carbamoyl]oximino]]-1,3-dithiolane.
4-[[O-[N-Methyl-N-(2,4-dimethyl-3-oxo-2-pentanesulfenyl)carbamoyl]oximino]]-1,3-dithiolane.
4-[[O-[N-Methyl-N-(2,4-dimethyl-3-oxo-2-pentanesulfenyl)carbamoyl]oximino]]-5,5-dimethyl-1,3-dithiolane.
2-[[O-[N-Methyl-N-(2-methyl-1-oxo-2-cyclopentanesulfenyl)carbamoyl]oximino]]-1,3-dithiolane.
2-[[O-[N-Methyl-N-(2,4,4-trimethyl-3-oxo-2-pentanesulfenyl)carbamoyl]oximino]]-1,3-dithiolane.
2-[[O-[N-Methyl-N-(2,4-dimethyl-3-oxo-2-pentanesulfenyl)carbamoyl]oximino]]-1,3,5-trithiane.
4-[[O-[N-Methyl-N-(2,4-dimethyl-3-oxo-2-pentanesulfenyl)carbamoyl]oximino]]-1,3,5-oxadithiane.
4-[[O-[N-Methyl-N-(2,4-dimethyl-3-oxo-2-pentanesulfenyl)carbamoyl]oximino]]-1,3-dithiolane.
4-[[O-[N-Methyl-N-(2,4-dimethyl-3-oxo-2-pentanesulfenyl)carbamoyl]oximino]]-5,5-dimethyl-1,3-dithiolane.
4-[[O-[N-Methyl-N-(2,4,4-trimethyl-3-oxo-2-pentanesulfenyl)carbamoyl]oximino]]-5-methyl-1,3-oxathiolane.
4-[[O-[N-Methyl-N-(2-benzoyl-2-propanesulfenyl)carbamoyl]oximino]]-5-methyl-1,3-oxathiolane.
3-[[O-[N-Methyl-N-(2,4-dimethyl-3-oxo-2-pentanesulfenyl)carbamoyl]oximino]]-2-methyl-1,4-oxathiane.
2-[[O-[N-Methyl-N-(2,4-dimethyl-3-oxo-2-pentanesulfenyl)carbamoyl]oximino]-4-methyl-tetrahydro-1,4-thiazin-3-one.
2-[[O-[N-Methyl-N-(2,4,4-trimethyl-3-oxo-2-pentanesulfenyl)carbamoyl]oximino]]-3,5,5-trimethyl-thiazolidin-4-one.
2-[[O-[N-Methyl-N-(2,4-dimethyl-3-oxo-2-pentanesulfenyl)carbamoyl]oximino]]-4,5,5-trimethylthiazolidin-3-one.
1-Methylthio-1-(N',N'-dimethylaminocarbonyl)formaldehyde O-[N-methyl-N-(2,4-dimethyl-3-oxo-2-pentanesulfenyl)carbamoyl]oxime.
7-[N-Methyl-N-(2,4,4-trimethyl-3-oxo-2-pentanesulfenyl)carbamoyloxy]-2,2-dimethyl-2,3-dihydrobenzofuran.
7-[N-Methyl-N-(2-benzoyl-2-propanesulfenyl)carbamoyloxy]-2,2-dimethyl-2,3-dihydrobenzofuran.
7-[N-Methyl-N-(2-methyl-1-oxo-2-cyclopentanesulfenyl)carbamoyloxy]-2,2-dimethyl-2,3-dihydrobenzofuran.
7-[N-Methyl-N-(3-formyl-3-pentanesulfenyl)carbamoyloxy]-2,2-dimethyl-2,3-dihydrobenzofuran.
1-[N-Methyl-N-(2,4-dimethyl-3-oxo-2-pentanesulfenyl)carbamoyloxy]-2-isopropoxybenzene.
1-[N-Methyl-N-(2,4-dimethyl-3-oxo-2-pentanesulfenyl)carbamoyloxy]-4-dimethylamino-3,5-xylene.
1-[N-Methyl-N-(2,4-dimethyl-3-oxo-2-pentanesulfenyl)carbamoyloxy]-4-methoxycarbonylamino-3,5-xylene.
1-[N-Methyl-N-(2,4-dimethyl-3-oxo-2-pentanesulfenyl)carbamoyloxy]-3-sec-butylbenzene.
1-[N-Methyl-N-(2,4-dimethyl-3-oxo-2-pentanesulfenyl)carbamoyloxy]-4-methylthio-3,5-xylene.
1-[N-Methyl-N-(2,4-dimethyl-3-oxo-2-pentanesulfenyl)carbamoyloxy]-2-(1,3-dioxolan-2-yl)-benzene.
1-[N-Methyl-N-(2,4-dimethyl-3-oxo-2-pentanesulfenyl)carbamoyloxy]-5,6,7,8-tetrahydronapthalene.
1-[N-Methyl-N-(2,4-dimethyl-3-oxo-2-pentanesulfenyl)carbamoyloxy]-2-chlorobenzene.
1-[N-Methyl-N-(2,4-dimethyl-3-oxo-2-pentanesulfenyl)carbamoyloxy]-3,5-di-t-butylbenzene.
1-[N-Methyl-N-(2,4-dimethyl-3-oxo-2-pentanesulfenyl)carbamoyloxy]-4-dimethylaminomethyleneiminobenzene.
1-[N-Methyl-N-(2,4-dimethyl-3-oxo-2-pentanesulfenyl)carbamoyloxy]-2-ethylthiomethylbenzene.
1-[N-Methyl-N-(2,4-dimethyl-3-oxo-2-pentanesulfenyl)carbamoyloxy]-2-(1,3-dithiolane-2-yl)-benzene.
1-[N-Methyl-N-(2,4,4-trimethyl-3-oxo-2-pentanesulfenyl)carbamoyloxy]-2,6-di-tert-butyl-4-(2,2-dicyanoethylidene)benzene.
2-[[O-[N-Methyl-N-(2,4-dimethyl-3-oxo-2-pentanesulfenyl)carbamoyl]-oximino]]-4-methyl-tetrahydro-1,4-thiazin-3-one.
2-[[O-[N-Methyl-N-(2,4-dimethyl-3-oxo-2-pentanesulfenyl)carbamoyl]oximino]]-3,3-dimethyl-tetrahydro-1,4-thiazin-5-one.
2-[[O-[N-Methyl-N-(2,4-dimethyl-3-oxo-2-pentanesulfenyl)carbamoyl]oximino]]-4-methyl-tetrahydro-1,4-oxazin-3-one.
1-Aminocarbonylmethylthioacetaldehyde O-[N-methyl-N-(2,4-dimethyl-3-oxo-2-pentanesulfenyl)carbamoyl]oxime.
2-Methylthio-2-methylpropionaldehyde O-[N-methyl-N-(2,4-dimethyl-3-oxo-2-pentanethiosulfenyl)carbamoyl]oxime.
2-Nitro-2-methylpropionaldehyde O-[N-methyl-N-(2,4-dimethyl-3-oxo-2-pentanethiosulfenyl)carbamoyl]oxime.
2-Cyano-2-methylpropionaldehyde O-[N-methyl-N-(2,4-dimethyl-3-oxo-2-pentanethiosulfenyl)carbamoyl]oxime.
2-Methylthio-2-methylpropionaldehyde O-[N-methyl-N-(2-benzoyl-2-propanethiosulfenyl)carbamoyl]oxime.
2-Methylsulfonyl-2-methylpropionaldehyde O-[N-methyl-N-(2-methyl-1-oxo-2-cyclopentanethiosulfenyl)carbamoyl]oxime.

1-Methylthio-3,3-dimethyl-2-butanone O-[N-methyl-N-(2,4-dimethyl-3-oxo-2-pentanethiosulfenyl)carbamoyl]oxime.

2-[[O-[N-Methyl-N-(2,4-dimethyl-3-oxo-2-pentanethiosulfenyl)carbamoyl]oximino]]-1,3-dithiolane.

2-[[O-[N-Methyl-N-(2-benzoyl-2-propanethiosulfenyl)carbamoyl]oximino]]-1,3-dithiolane.

2-[[O-[N-Methyl-N-(2,4-dimethyl-3-oxo-2-pentanethiosulfenyl)carbamoyl]oximino]]-1,3,5-trithiane.

4-[[O-[N-Methyl-N-(2,4,4-trimethyl-3-oxo-2-pentanethiosulfenyl)carbamoyl]oximino]]-1,3-dithiolane.

4-[[O-[N-Methyl-N-(2,4-dimethyl-3-oxo-2-pentanethiosulfenyl)carbamoyl]oximino]]-5-methyl-1,3-dithiolane.

4-[[O-[N-Methyl-N-(2-benzoyl-2-propanethiosulfenyl)carbamoyl]oximino]]-5-methyl-1,3-oxathiolane.

2-[[O-[N-Methyl-N-(2,4-dimethyl-3-oxo-2-pentanethiosulfenyl)carbamoyl]oximino]]-4-isopropyl-tetrahydro-1,4-thiazin-3-one.

2-[[O-[N-Methyl-N-(2,4-dimethyl-3-oxo-2-pentanethiosulfenyl)carbamoyl]oximino]]3,5,5-trimethylthiazolidin-4-one.

2-[[O-[N-Methyl-N-(2-benzoyl-2-propanethiosulfenyl)carbamoyl]oximino]]-3,5,5-trimethylthiazolidin-4-one.

2-[[O-[N-Methyl-N-(2,4-dimethyl-3-oxo-2-pentanethiosulfenyl)carbamoyl]oximino]]-4,5,5-trimethylthiazolidin-3-one.

1-Methylthio-1-(N',N',-dimethylaminocarbonyl)formaldehyde O-[N-methyl-N-(2,4-dimethyl-3-oxo-2-pentanethiosulfenyl)carbamoyl]oxime.

7-[N-Methyl-N-(2,4-dimethyl-3-oxo-2-pentanethiosulfenyl)carbamoyloxy]-2,2-dimethyl-2,3-dihydrobenzofuran.

7-[(N-Methyl-N-(2-benzoyl-2-propanethiosulfenyl)carbamoyloxy]-2,2-dimethyl-2,3-dihydrobenzofuran.

7-[N-Methyl-N-(2-methyl-1-oxo-2-cyclopentanethiosulfenyl)carbamoyloxy]-2,2-dimethyl-2,3-dihydrobenzofuran.

1-[N-Methyl-N-(2,4-dimethyl-3-oxo-2-pentanethiosulfenyl)carbamoyloxy]-2-isopropoxybenzene.

1-[N-Methyl-N-(2,4-dimethyl-3-oxo-2-pentanethiosulfenyl)carbamoyloxy]napthalene.

1[N-Methyl-N-(2,4-dimethyl-3-oxo-2-entanethiosulfenyl)carbamoyloxy]-4-dimethylamino-3-methylbenzene.

1-[N-Methyl-N-(2,4-dimethyl-3-oxo-2-pentanethiosulfenyl)carbamoyloxy]-3,5-di-t-butylbenzene.

1-[N-Methyl-N-(2,4,4-trimethyl-3-oxo-2-pentanethiosulfenyl)carbamoyloxy]-2-(1,3-dioxolan-2yl)-benzene.

1-[N-Methyl-N-(2-benzoyl-2-propanethiosulfenyl)carbamoyloxy]-4-methylthio-3-methylbenzene.

2-[[O-[N-Methyl-N-(2,4-dimethyl-3-oxo-2-pentanethiosulfenyl)carbamoyl]oximino]]-4-methyl-tetrahydro-1,4-thiazin-3-one.

2-[[O-[N-Methyl-N-(2-benzoyl-2-propanethiosulfenyl)carbamoyl]oximino]]-3-methyl-tetrahydro-1,4-thiazin-5-one.

2-[[O-[N-Methyl-N-(2,4-dimethyl-3-oxo-2-pentanethiosulfenyl)carbamoyl]oximino]]-4-iospropyl-tetrahydro-1,4-oxazin-3-one.

1-Dimethylaminocarbonylmethylthioacetaldehyde O-[N-methyl-N-(2,4-dimethyl-3-oxo-2-pentanethiosulfenyl)carbamoyl]oxime.

4-[N-Methyl-N-(2,4-dimethyl-3-oxo-2-pentanethiosulfenyl)carbamoyloxy]-benzothiene.

7[N-Methyl-N-(2-benzoyl-2-propanesulfenyl)carbamoyloxy]indan.

1-[N-Methyl-N-(2,4-dimethyl-3-oxo-2-pentanesulfenyl)carbamoyloxy]-3-propynyloxy-benzene.

1-[N-Methyl-N-(2,4-dimethyl-3-oxo-2-pentanesulfenyl)carbamoyloxy]-3-methyl-4-nitrobenzene.

1-[N-Methyl-N-(2,4-dimethyl-3-oxo-2-pentanethiosulfenyl)carbamoyloxy]-4-cyanobenzene.

1[N-Methyl-N-(2,4-dimethyl-3-oxo-2-pentanesulfenyl)carbamoyloxy]-2-ethyl.

1-Methylthioacetaldehyde-O-[N-methyl-N-(2,4-dimethyl-3-oxo-2-pentanethiosulfenyl)carbamoyl]oxime.

1-(2-Cyanoethylthio)acetaldehyde-O-[N-methyl-N-(2,4-dimethyl-3-oxo-2-pentanethiosulfenyl)carbamoyl]oxime.

2-[O-[N-Methyl-N-(2,4-dimethyl-3-oxo-2-pentanethiosulfenyl)carbamoyl]oximino]-1,3,5-trithiane-5-oxide.

4-[O-[N-Hexyl-N-(2,4-dimethyl-3-oxo-2-pentanethiosulfenyl)carbamoyl]oximino]-1,3,5-oxadithianesulfonyl methylbenzene.

Selected species of the new compounds were evaluated to determine their pesticidal activity against nematodes, mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig, air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead.

Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80° ±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper, Five randomly selected larvae were introduced into each dish and the dishes were closed. The closed dishes were labeled and held at 80°-85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80° ±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dished were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243-244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer above five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and numphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

Nematocide Test

The test organism used was the infective migratory larvae of the root-knot nematode, *Meloidogyne incognita* var. *acrita*, reared in the greenhouse on roots of cucumber plants. Infected plants were removed from the culture, and the roots are chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone addition of an emulsifier, and dilution with water. Primary screening tests were conducted at 3.33 m.g. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots, and the amount of galling visually rated.

The results of these tests are set forth in Table I below. In these tests the pesticidal activity of the compounds against aphid, mite, Southern Armyworm, Bean Beetle and house fly was rated as follows:
A=excellent control
B=partial control
C=no control In the test for activity against nematodes activity was rated as follows:
1=severe galling, equal to untreated plants
2=moderate galling
3=light galling
4=very light galling
5=no galling, perfect control
Dashes indicate no test conducted.

Certain of these compositions were also evaluated to determine their peroral toxicity to mammals. The animal selected for this experiment was the rat. The test results obtained are expressed in terms of the number of milligrams of compositions per kilogram of weight of the animal required to achieve a mortality rate of 50 percent ($LD_{50}$).

The results of all of these tests are set forth in Table I below:

TABLE I

BIOLOGICAL ACTIVITY

| STRUCTURE | APHID | MITE | S. ARMY-WORM | M. BEAN BEETLE | H. FLY | NEMA-TODES | A.O. RAT. mg/kg |
|---|---|---|---|---|---|---|---|
| CH₃—C(=NOCN(CH₃)(S-C(CH₃)₂-C(O)-CH(CH₃)₂))—SCH₃ | A | C | A | A | A | 1 | 134 |
| CH₃—C(=NOCN(CH₃)(S-C(CH₃)₂-C(O)-CH(CH₃)₂))—S-CH(CH₃)₂ | A | A | A | A | A | 3 | 37 |
| CH₃-S-C(CH₃)₂-CH—C(=NOCN(CH₃)(S-C(CH₃)₂-C(O)-CH(CH₃)₂)) | A | A | C | B | A | 3 | — |
| O₂N-C(CH₃)₂-CH=C(NOCN(CH₃)(S-C(CH₃)₂-C(O)-CH(CH₃)₂)) | A | A | A | A | A | — | 12 |
| (dithiane)=N-OCN(CH₃)(S-C(CH₃)₂-C(O)-CH(CH₃)₂) | A | A | A | A | A | 3 | — |
| (CH₃, oxathiolane)=NOCN(CH₃)(S-C(CH₃)₂-C(O)-CH(CH₃)₂) | A | C | A | A | A | — | 16 |
| (CH₃N, O=C, S thiazolidinone)=NOCN(CH₃)(S-C(CH₃)₂-C(O)-CH(CH₃)₂) | C | C | A | A | C | — | 226 |

TABLE I-continued

| STRUCTURE | BIOLOGICAL ACTIVITY | | | | | | |
|---|---|---|---|---|---|---|---|
| | APHID | MITE | S. ARMY-WORM | M. BEAN BEETLE | H. FLY | NEMA-TODES | A.O. RAT. mg/kg |
| (structure 1) | C | B | A | A | A | — | — |
| (structure 2) | B | C | A | A | A | 3 | — |
| (structure 3) | C | C | A | A | C | — | — |
| (structure 4) | C | C | A | A | C | — | — |
| (structure 5) | C | C | C | C | A | 3 | — |
| (structure 6) | A | B | A | A | A | | 31 |
| (structure 7) | A | C | A | A | A | | — |
| (structure 8) | A | B | A | A | A | 3 | 226 |
| (structure 9) | A | A | A | A | A | 4 | 42 |
| (structure 10) | A | A | A | A | A | 3 | 8 |

TABLE I-continued

| STRUCTURE | BIOLOGICAL ACTIVITY | | | | | | A.O. RAT. mg/kg |
|---|---|---|---|---|---|---|---|
| | APHID | MITE | S. ARMY-WORM | M. BEAN BEETLE | H. FLY | NEMA-TODES | |
| 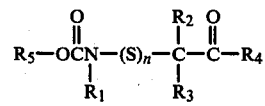 | A | A | A | A | A | 5 | 20 |
| 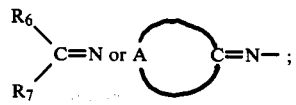 | A | B | A | A | A | | 226 |

The compounds contemplated in this invention may be applied as insecticides, miticides and nematocides according to methods known to those skilled in the art. Pesticidal compositions containing the compounds as the active toxicant will usually comprise a carrier and-/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre.

The pesticides contemplated herein prevent attack by insects, nematodes and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

What is claimed is:

1. A compound of the formula:

$$R_5-O\overset{O}{\overset{\|}{C}}\underset{R_1}{N}-(S)_n-\overset{R_2}{\underset{R_3}{C}}-\overset{O}{\overset{\|}{C}}-R_4$$

wherein:

n is 1 or 2;

$R_1$ is alkyl;

$R_2$ is alkyl or chlorine;

$R_3$ is hydrogen, alkyl, phenyl, alkoxycarbonyl, alkanoyl or phenoxycarbonyl;

$R_4$ is hydrogen, phenoxy, alkyl, alkoxy or phenyl;

$R_3$ and $R_4$ together may form an alkylene chain completing a five or six membered alicyclic ketone or dione;

$R_5$ is:

A. naphthyl, benzofuranyl, benzothienyl, indanyl or phenyl; or

B. phenyl substituted with one or more chloro, bromo, fluoro, nitro, cyano, alkyl, alkynyloxy, alkoxy, dioxalanyl, dialkylamino, alkoxycarbonylamino, dicyanoethylidene, alkylthio, alkylthioalkyl, alkylsulfinylalkyl, alkylsulfonylalkyl, dithiolanyl or dialkylaminomethyleneimino groups; or C. $\underset{R_7}{\overset{R_6}{\diagdown}}C=N$ or $A\bigcirc C=N-$ ;

$R_6$ and $R_7$ are individually hydrogen, cyano, chloro, alkyl, phenyl, alkylthio, alkylthioalkyl, alkylsulfinylalkyl, alkylsulfonylalkyl, cyanoalkyl, nitroalkyl, cyanoalkylthio alkanoyl or aminocarbonylalkylthio groups; and A is a divalent alkylene chain completing a five or six membered alicyclic ring which includes up to three hetero atoms selected from among oxygen, sulfur, sulfinyl, sulfonyl, aminocarbonyl or alkylaminocarbonyl provided that not more than one of said hetero atoms may be aminocarbonyl or alkylaminocarbonyl;

with the proviso that:
- A. The total number of aliphatic carbon atoms included in $R_1$, $R_2$, $R_3$, $R_4$, $R_6$ and $R_7$ individually may not exceed six; and
- B. At least one $R_3$ or $R_5$, substituent includes an oxocarbonyl, heterocyclic function or cyano group.

2. A compound according to claim 1 wherein $R_1$ is methyl and the total number of aliphatic carbons included in any one $R_2$, $R_3$, $R_4$, $R_6$ or $R_7$ substituent may not exceed four.

3. A compound according to claim 1 wherein n is 1.
4. A compound according to claim 1 wherein n is 2.
5. A compound according to claim 1 wherein $R_1$ is methyl.
6. A compound according to claim 1 wherein $R_1$ is methyl.
7. A compound according to claim 1 wherein $R_2$ is alkyl.
8. A compound according to claim 1 wherein $R_2$ is methyl.
9. A compound according to claim 1 wherein $R_3$ and $R_4$ are alkyl.
10. A compound according to claim 1 wherein $R_3$ and $R_4$ are phenyl.
11. A compound according to claim 1 wherein $R_4$ is isopropyl.
12. A compound according to claim 1 wherein $R_3$ is methyl.
13. A compound according to claim 1 wherein $R_5$ is naphthyl, benzofuranyl, phenyl or substituted phenyl.
14. A compound according to claim 1 wherein $R_6$ and $R_7$ are individually hydrogen, cyano, alkyl, alkylthio, alkylthioalkyl, alkylsulfinylalkyl, alkylsulfonylalkyl, cyanoalkyl, nitroalkyl or cyanoalkylthio.
15. A compound according to claim 1 wherein A is a divalent aliphatic chain completing a 1,4-dithiane, 1,3-dithiolane, 1,4-thiazine-3-one, 1,4-oxazine-3-one, 1,3-5-trithiane, 1,3,5-oxadithiane, 1,4-oxathiane, 1,3-oxathiolane, 1,3-thiazolidin-4-one, or thiophane ring wherein sulfur may be in any of its oxidation states or in any combination thereof.
16. 2-[[0-[N-Methyl-N-(2,4-dimethyl-3-oxo-2-pentanesulfenyl) carbamoyl]] -1,4-dithiane.
17. 7[N-Methyl-N-(2,4-dimethyl-3-oxo-2-pentanesulfenyl)carbamoyloxy]-2,2-dimethyl-2,3-dihydrobenzofuran.
18. An insecticidal, miticidal and nematocidal composition comprising an acceptable carrier and an insecticidally, miticidally or nematocidally effective amount of a compound of the formula:

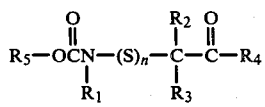

wherein:
n is 1 or 2;
$R_1$ is alkyl;
$R_2$ is alkyl or chlorine;
$R_3$ is hydrogen, alkyl, phenyl, alkoxycarbonyl, alkanoyl or phenoxycarbonyl;
$R_4$ is hydrogen, phenoxy, alkyl, alkoxy or phenyl;
$R_3$ and $R_4$ together may form an alkylene chain completing a five or six membered alicyclic ketone or dione;
$R_5$ is:
- A. naphthyl, benzofuranyl, benzothienyl, indanyl or phenyl; or
- B. phenyl substituted with one or more chloro, bromo, fluoro, nitro, cyano, alkyl, alkynyloxy, alkoxy, dioxalanyl, dialkylamino, alkoxycarbonylamino, dicyanoethylidene, alkylthio, alkylthioalkyl, alkylsulfinylalkyl, alkylsulfonylalkyl, dithiolanyl or dialkylaminomethyleneimino groups; and

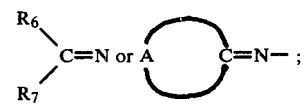    C.

wherein:
$R_6$ and $R_7$ are individually hydrogen, cyano, chloro, alkyl, phenyl, alkylthio, alkylthioalkyl, alkylsulfinylalkyl, alkylsulfonylalkyl, cyanoalkyl, nitroalkyl, cyanoalkylthio alkanoyl or aminocarbonylalkylthio groups; and D. A is a divalent alkylene chain completing a five or six membered alicyclic ring which includes up to three hetero atoms selected from among oxygen, sulfur, sulfinyl, sulfonyl, aminocarbonyl or alkylaminocarbonyl provided that not more than one of said hetero atoms may be aminocarbonyl or alkylaminocarbonyl;

With the proviso that:
- A. The total number of aliphatic carbon atoms included in $R_1$, $R_2$, $R_3$, $R_4$, $R_6$ and $R_7$ substituents individually may not exceed six; and
- B. At least one $R_3$ or $R_5$, substituent includes an oxocarbonyl group, a heterocyclic group or a cyano group.

19. A composition according to claim 18 wherein n is 1.
20. A composition according to claim 18 wherein n is 2.
21. A composition according to claim 18 wherein $R_1$ is methyl.
22. A composition according to claim 18 wherein $R_2$ is alkyl.
23. A composition according to claim 18 wherein $R_2$ is methyl.
24. A composition according to claim 18 wherein $R_3$ and $R_4$ are alkyl.
25. A composition according to claim 18 wherein $R_3$ and $R_4$ are phenyl.
26. A composition according to claim 18 wherein $R_4$ is isopropyl.
27. A composition according to claim 18 wherein $R_3$ is methyl.
28. A composition according to claim 18 wherein $R_5$ is naphthyl, benzofuranyl, phenyl or substituted phenyl.

29. A composition according to claim 18 wherein $R_6$ and $R_7$ are individually hydrogen, cyano, alkyl, alkylthio, alkylthioalkyl, alkylsulfinylalkyl, alkylsulfonylalkyl, cyanoalkyl, nitroalkyl or cyanoalkylthio.

30. A composition according to claim 18 wherein A is a divalent aliphatic chain completing a 1,4-dithiane, 1,3-dithiolane, 1,4-thiazine-3one, 1,4-oxazine-3-one, 1,3,5-trithiane, 1,3,5-oxadithiane, 1,4-oxathiane, 1,3-oxathiolane, 1,3-thiazolidin-4-one, or thiophane ring wherein sulfur may be in any of its oxidation states or in any combination thereof.

31. A composition according to claim 18 wherein the active toxicant is 2-[[0-[N-Methyl-N-(2,4-dimethyl-3-oxo-2-pentane-sulfenyl) carbamoyl]oximino]]-1,4-dithiane.

32. A composition according to claim 18 wherein the active toxicant is 7-[N-Methyl-N-(2,4-dimethyl-3-oxo-2-pentanesulfenyl) carbamoyloxy]-2,2-dimethyl-2,3-dihydrobenzofuran.

33. A method of controlling insects, mites and nematodes which comprises subjecting them to an insecticidally, miticidally or nematocidally effective amount of a compound of the formula:

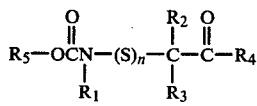

wherein:
n is 1 or 2;
$R_1$ is alkyl;
$R_2$ is alkyl or chlorine;
$R_3$ is hydrogen, alkyl, phenyl, alkoxycarbonyl, alkanoyl or phenoxycarbonyl;
$R_4$ is hydrogen, phenoxy, alkyl, alkoxy or phenyl;
$R_3$ and $R_4$ together may form an alkylene chain completing a five or six membered alicyclic ketone or dione;
$R_5$ is:
A. naphthyl, benzofuranyl, benzothienyl, indanyl or phenyl; or
B. phenyl substituted with one or more chloro, bromo, fluoro, nitro, cyano, alkyl, alkynyloxy, alkoxy, dioxalanyl, dialkylamino, alkoxycarbonylamino, dicyanoethylidene, alkylthio, alkylthioalkyl, alkylsulfinylalkyl, alkylsulfonylalkyl, dithiolanyl or dialkylaminomethyleneimino groups; and

C.

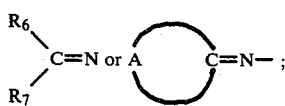

$R_6$ and $R_7$ are individually hydrogen, cyano, chloro, alkyl, phenyl, alkylthio, alkylthioalkyl, alkylsulfinylalkyl, alkylsulfonylalkyl, cyanoalkyl, nitroalkyl, cyanoalkylthio alkanoyl or aminocarbonylalkylthio groups; and D. A is a divalent alkylene chain completing a five or six membered alicyclic ring which includes up to three hetero atoms selected from among oxygen, sulfur, sulfinyl, sulfonyl, aminocarbonyl or alkylaminocarbonyl provided that no more than one of said hetero atoms may be aminocarbonyl or alkylaminocarbonyl;

With the proviso that:
A. The total number of aliphatic carbon atoms included in $R_1$, $R_2$, $R_3$, $R_4$, $R_6$ and $R_7$ substituents individually may not exceed six; and
B. At least one $R_3$ or $R_5$, substituents includes a oxocarbonyl group, a heterocyclic group, or a cyano group.

34. A method according to claim 33 wherein n is 1.

35. A method according to claim 33 wherein n is 2.

36. A method according to claim 33 wherein $R_1$ is methyl.

37. A method according to claim 33 wherein $R_2$ is alkyl.

38. A method according to claim 33 wherein $R_2$ is methyl.

39. A method according to claim 33 wherein $R_3$ and $R_4$ are alkyl.

40. A method according to claim 33 wherein $R_3$ and $R_4$ are phenyl.

41. A method according to claim 33 wherein $R_4$ is isopropyl.

42. A method according to claim 33 wherein $R_3$ is methyl.

43. A method according to claim 33 wherein $R_5$ is naphthyl, benzofuranyl, phenyl or substituted phenyl.

44. A method according to claim 33 wherein $R_6$ and $R_7$ are individually hydrogen, cyano, alkyl, alkylthio, alkylthioalkyl, alkylsulfinylalkyl, alkylsulfonylalkyl, cyanoalkyl, nitroalkyl or cyanoalkylthio.

45. A method according to claim 33 wherein A is a divalent aliphatic chain completing a 1,4-dithiane, 1,3-dithiolane, 1,4-thiazine-3-one, 1,4-oxazine-3-one, 1,3,5-trithiane, 1,3,5-oxadithiane, 1,4-oxathiane, 1,3-oxathiolane, 1,3-thiazolidin-4-one, or thiophene ring wherein sulfur may be in any of its oxidation states or in any combination thereof.

46. A method according to claim 33 wherein the compound is 2-[[0-[N-Methyl-N-(2,4-dimethyl-3-oxo-2-pentanesulfenyl)carbamoyl]oximino]]-1,4-dithiane.

47. A method according to claim 33 wherein the compound is 7-[N-Methyl-N-(2,4-dimethyl-3-oxo-2-pentane-sulfenyl) carbamoyloxy]-2,2-dimethyl-2,3-dihydrobenzofuran.

* * * * *

UNITED STATES PATENT AND TRADEMARK OFFICE
CERTIFICATE OF CORRECTION

PATENT NO. : 4,179,514

DATED : Dec. 18, 1979

INVENTOR(S) : T.D.J. D'Silva

It is certified that error appears in the above-identified patent and that said Letters Patent are hereby corrected as shown below:

Column 4, line 50 "3-oxo  B   2-" should read -- 3-oxo-2- --.

Column 4, line 64 "2.99" should read -- 2.29 --.

Column 7, lines 17-25. The formula reads as follows:

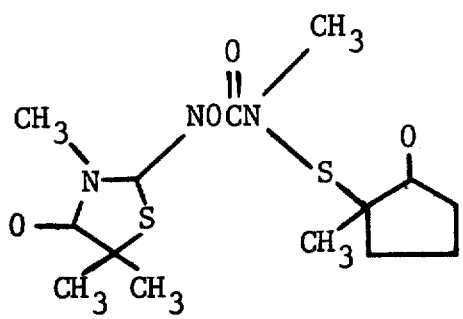

but should read as follows:

UNITED STATES PATENT AND TRADEMARK OFFICE
CERTIFICATE OF CORRECTION

PATENT NO. : 4,179,514
DATED : Dec. 18, 1979
INVENTOR(S) : T.D.J. D'Silva

It is certified that error appears in the above-identified patent and that said Letters Patent are hereby corrected as shown below:

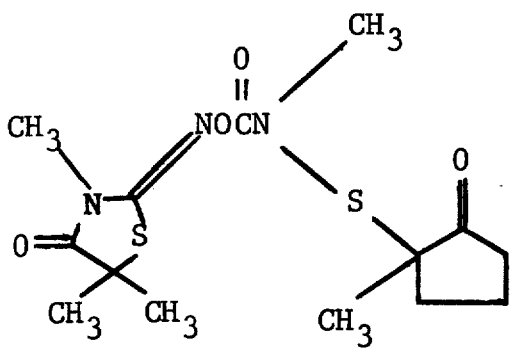

Column 7, lines 47-55. The formula reads as follows:

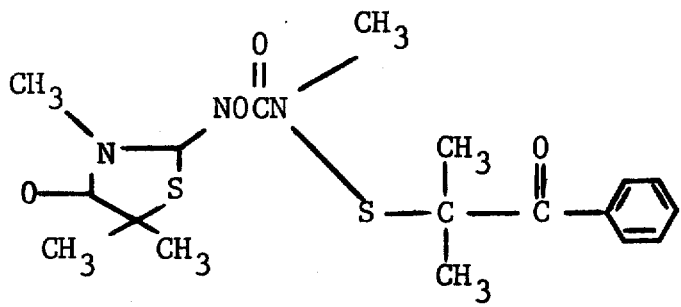

but should read as follows:

UNITED STATES PATENT AND TRADEMARK OFFICE
CERTIFICATE OF CORRECTION

PATENT NO. : 4,179,514
DATED : Dec. 18, 1979
INVENTOR(S) : T.D.J. D'Silva

It is certified that error appears in the above–identified patent and that said Letters Patent are hereby corrected as shown below:

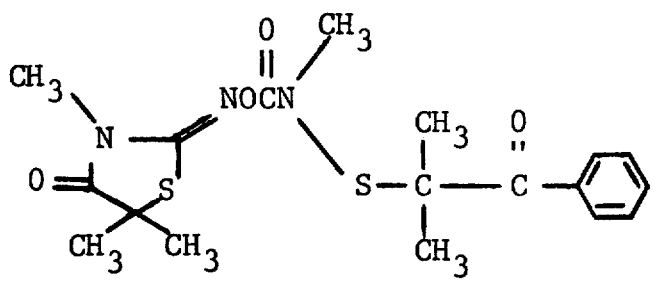

Signed and Sealed this

Twenty-second Day of April 1980

[SEAL]

Attest:

Attesting Officer

SIDNEY A. DIAMOND

Commissioner of Patents and Trademarks